(12) United States Patent
Tagawa (10) Patent No.: US 9,011,000 B2
(45) Date of Patent: Apr. 21, 2015

(54) X-RAY IMAGING APPARATUS

(75) Inventor: Motoki Tagawa, Chigasaki (JP)

(73) Assignee: Canon Kabushiki Kaisha, Tokyo (JP)

(*) Notice: Subject to any disclaimer, the term of this patent is extended or adjusted under 35 U.S.C. 154(b) by 265 days.

(21) Appl. No.: 13/613,296

(22) Filed: Sep. 13, 2012

(65) Prior Publication Data

US 2013/0077763 A1   Mar. 28, 2013

(30) Foreign Application Priority Data

Sep. 27, 2011 (JP) ................................. 2011-211128

(51) Int. Cl.
G03B 42/04 (2006.01)
A61B 6/00 (2006.01)
H05G 1/02 (2006.01)
A61B 6/10 (2006.01)

(52) U.S. Cl.
CPC .............. *A61B 6/4283* (2013.01); *H05G 1/02* (2013.01); *A61B 6/10* (2013.01); *G03B 42/04* (2013.01)

(58) Field of Classification Search
CPC ........ A61B 6/08; A61B 6/542; A61B 6/4441; G01N 23/04; F27B 9/30; F27D 21/0035; F27D 2201/00; G03B 42/04; H01J 35/08
USPC .............. 378/62, 87, 98, 98.8, 167, 169, 182, 378/189; 250/370.9, 370.09
See application file for complete search history.

(56) References Cited

U.S. PATENT DOCUMENTS

| | | | |
|---|---|---|---|
| 7,821,782 B2 | 10/2010 | Doherty et al. | |
| 2007/0138400 A1* | 6/2007 | Ertel et al. | 250/370.11 |
| 2009/0116620 A1* | 5/2009 | Kato | 378/167 |
| 2010/0183123 A1* | 7/2010 | Thiery et al. | 378/187 |
| 2012/0168626 A1* | 7/2012 | Namekawa | 250/336.1 |

FOREIGN PATENT DOCUMENTS

| | | |
|---|---|---|
| CN | 1540442 A | 10/2004 |
| CN | 101808583 A | 8/2010 |
| DE | 3711732 A1 | 7/1988 |
| EP | 1471384 B1 | 12/2012 |
| JP | 2005006806 A | 1/2005 |
| JP | 2005-195643 A | 7/2005 |
| JP | 2006006424 A | 1/2006 |
| JP | 3848288 B2 | 11/2006 |
| WO | 2011/037153 A1 | 3/2011 |

* cited by examiner

*Primary Examiner* — Glen Kao
*Assistant Examiner* — Julio M Duarte-Carvajalin
(74) *Attorney, Agent, or Firm* — Canon USA Inc. IP Division

(57) ABSTRACT

An X-ray imaging apparatus includes an X-ray sensor configured to convert an X-ray to an image signal, a supporting member configured to support the X-ray sensor, and a casing having the X-ray sensor and the supporting member incorporated therein, wherein the casing includes a front casing configured to cover a front surface of the X-ray imaging apparatus where an X-ray enters, and a rear casing configured to cover a rear surface opposite the front surface of the X-ray imaging apparatus, and wherein a recess is formed toward the exterior of the casings at the connection portion of the front casing and the rear casing.

8 Claims, 7 Drawing Sheets

ELEVATIONAL VIEW OF X-RAY IMAGING APPARATUS

CROSS SECTIONAL VIEW TAKEN ALONG B-B LINE
(SIDE CROSS SECTIONAL VIEW)

FIG. 1A

ELEVATIONAL VIEW OF X-RAY IMAGING APPARATUS

FIG. 1B

CROSS SECTIONAL VIEW TAKEN ALONG A-A LINE

FIG. 2A

CROSS SECTIONAL VIEW TAKEN ALONG B-B LINE
(SIDE CROSS SECTIONAL VIEW)

FIG. 2B

CROSS SECTIONAL VIEW TAKEN ALONG C-C LINE
(CROSS SECTIONAL VIEW OF CORNER PORTION)

CROSS SECTIONAL VIEW TAKEN ALONG D-D LINE
(CROSS SECTIONAL VIEW OF PORTABLE GRIPPING PORTION)

FIG. 4B

CROSS SECTIONAL VIEW TAKEN ALONG E-E LINE
(CROSS SECTIONAL VIEW OF CORNER
PORTION ON GRIPPING PORTION SIDE)

X-RAY IMAGING APPARATUS

BACKGROUND OF THE INVENTION

1. Field of the Invention

The present invention relates to a portable X-ray imaging apparatus.

2. Description of the Related Art

In recent years, an apparatus that acquires digital images using semiconductor sensors has been extensively used as an X-ray imaging apparatus for medical image diagnosis and nondestructive inspection. Such an apparatus enables image acquisition in a way different from the conventional one using a photographic sensitive film, and an operator using the apparatus can immediately check acquisition of images, leading to improvement in work efficiency. The apparatus also covers a very wide dynamic range, resulting in the imaging that is not affected by a variable exposure amount of an X-ray.

As discussed in Japanese Patent No. 3848288, the progress of the reduction in size and weight of the apparatus enables practical use of the portable apparatus. The portable apparatus allows image acquisition of a patient at any attitude, and is readily used for X-ray imaging in a general hospital room and outside thereof.

Unfortunately, operators sometimes drop such a portable X-ray imaging apparatus due to carelessness while carrying it. The drop can be supposed to occur mostly from a height of about 0.5 to 1 m, from consideration of the height of a table and the height of a position the apparatus is carried at. Thus, the apparatus needs to have a sufficient mechanical strength.

Meanwhile, the apparatus generally cannot reduce the weight to less than 2.5 kg because it has electrical circuits configured to drive sensors incorporated therein. The weight causes a large impact energy on the apparatus when dropped. The X-ray imaging apparatus is sometimes placed under a subject for imaging. To reduce the uncomfortable physical contact of the apparatus given to the subject, a thin apparatus is common having a thickness of about 15 mm. Therefore, it is also difficult to increase rigidity and resistance to dropping of the X-ray imaging apparatus.

Japanese Patent Application Laid-Open No. 2006-006424 discusses an X-ray imaging apparatus provided with a buffer material on the sides thereof for impact absorption to secure an adequate strength. Further, Japanese Patent Application Laid-Open No. 2005-006806 discusses a protection frame for an X-ray imaging apparatus. The frame is used instead of the buffer material that increases the size of the apparatus, and is attached to the outside of a casing of the apparatus when it is carried.

SUMMARY OF THE INVENTION

The present invention relates to a portable X-ray imaging apparatus having a sufficient mechanical strength without increase in the external size thereof.

According to an aspect of the present invention, an X-ray imaging apparatus includes an X-ray sensor configured to convert an X-ray to an image signal, a supporting member configured to support the X-ray sensor, and a casing having the X-ray sensor and the supporting member incorporated therein, wherein the casing includes a front casing configured to cover a front surface of the X-ray imaging apparatus where an X-ray enters, and a rear casing configured to cover a rear surface opposite the front surface of the X-ray imaging apparatus, and wherein a recess is formed toward the exterior of the casings at the connection portion of the front casing and the rear casing.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

DESCRIPTION OF THE EMBODIMENTS

Various exemplary embodiments, features, and aspects of the invention will be described in detail below with reference to the drawings.

Figure 1A:
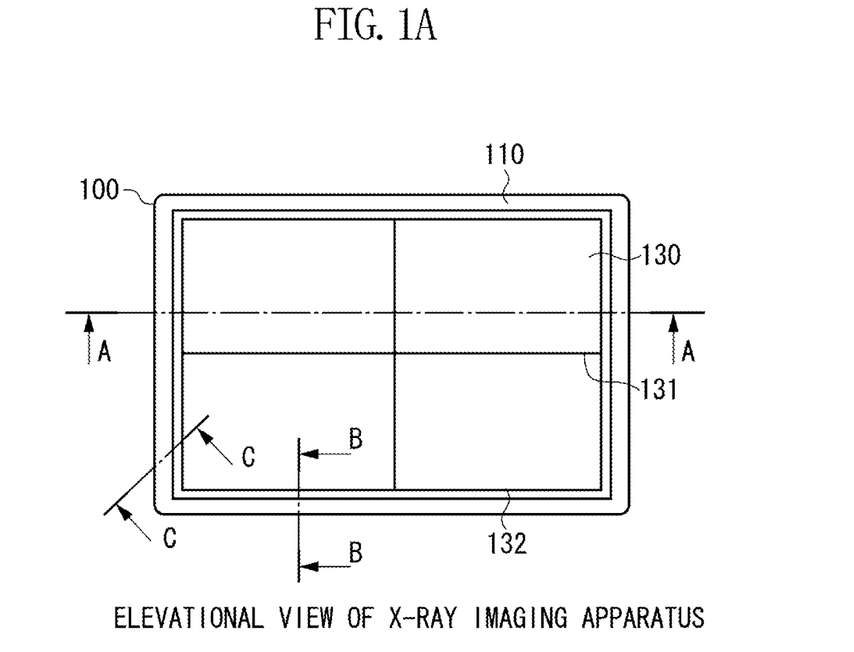
FIGS. 1A and 1B illustrate an X-ray imaging apparatus according to a first exemplary embodiment of the present invention.
Figure 1B:
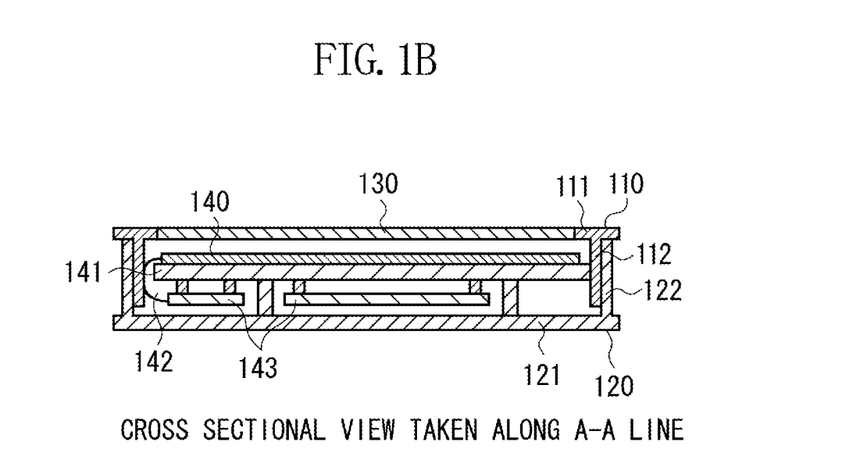

FIGS. 1A and 1B illustrate a portable X-ray imaging apparatus 100 according to a first exemplary embodiment of the present invention. FIG. 1A is an elevational view seen from an X-ray incidence surface. FIG. 1B is a cross sectional view taken along the line A-A in FIG. 1A.

To capture an X-ray image, a subject is positioned between an X-ray generator (not illustrated) and the X-ray imaging apparatus 100, so that the X-ray imaging apparatus 100 reads an X-ray transmitted through the subject to obtain image information. The X-ray imaging apparatus 100 includes an X-ray sensor panel 140 incorporated therein. The X-ray sensor panel 140 includes a glass substrate on which a photoelectric conversion element and a phosphor are laminated.

Irradiated by the X-ray, the phosphor in the X-ray sensor panel 140 emits light, and the light is converted into an electrical signal as an image signal by the photoelectric conversion element of the panel 140. The X-ray sensor panel 140 has a rigid supporting member 141 attached to a surface thereof on the opposite surface of an X-ray incident surface. The rigid supporting member 141 prevents deformation and breakage of the X-ray sensor panel 140 due to an external load and vibration during carriage of the X-ray imaging apparatus 100.

The X-ray sensor panel 140 further has a buffer sheet (not illustrated) between the X-ray incident surface and the casing of the X-ray imaging apparatus 100. The buffer sheet prevents breakage of the X-ray sensor panel 140 due to a load applied from the X-ray incidence surface.

The X-ray sensor panel 140 is connected to an electric circuit board 143 via a flexible circuit board 142. The electric circuit board 143 controls the X-ray sensor panel 140, and processes the image signal. The supporting member 141 also serves to fix the electric circuit board 143. The supporting member 141 has a rib to support the casing and to prevent direct application of a load onto the electric circuit board 143 from the rear surface of the casing.

The casing of the X-ray imaging apparatus 100 includes a front casing 110, a rear casing 120, and an X-ray transmission plate 130. The front casing 110 includes a front planer portion 111 and a side wall portion 112. Similarly, the rear casing 120 includes a rear planer portion 121 and a side wall portion 122. The front casing 110 and the rear casing 120 are made of a low specific gravity material, such as aluminum and magnesium, to have a sufficient strength against dropping and shock, and a reduced weight for easy carriage.

To form a complicated structure, the casings 110 and 120 may desirably be made by die casting. The front planer portion 111 has the X-ray transmission plate 130 at a position corresponding to an X-ray reading area. The X-ray transmission plate 130 may be made of carbon fiber reinforced plastic (CFRP), for example.

The X-ray transmission plate 130 has indexes 131, 132 used to identify a reading center of the X-ray sensor panel 140 and a reading area of the X-ray sensor panel 140. The outer side wall of the X-ray imaging apparatus 100 is formed with the side wall portions 111 and 121 of the front casing 110 and the rear casing 120 respectively in an overlapped manner.

The structure can increase the height of the side walls of the front casing 110 and the rear casing 120 respectively, thereby enabling the bending rigidity of the side walls to be increased. Further, the side walls also can prevent entrance of light to the inside of the X-ray imaging apparatus 100 from the outside.

If accidentally dropped, the X-ray imaging apparatus 100 often hits a floor at a side or a corner thereof. Accordingly, the peripheral edge portions of the X-ray imaging apparatus 100 need to have a high shock resistant property. In a case where the casings 110 and 120 are deformed due to insufficient shock resistant property, light may enter the inside of the X-ray imaging apparatus 100, resulting in poor quality of images. The deformation otherwise may cause increase in thickness of part of the casings 110 and 120, so that the X-ray imaging apparatus 100 cannot be placed in a mount.

Figure 2A:
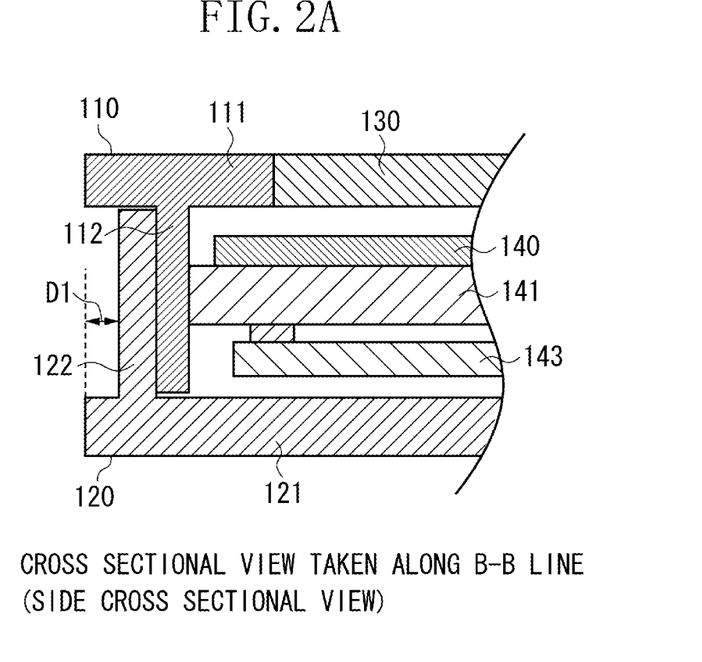
FIGS. 2A and 2B are cross sectional views each illustrating a peripheral edge portion of the X-ray imaging apparatus according to the first exemplary embodiment.
Figure 2B:
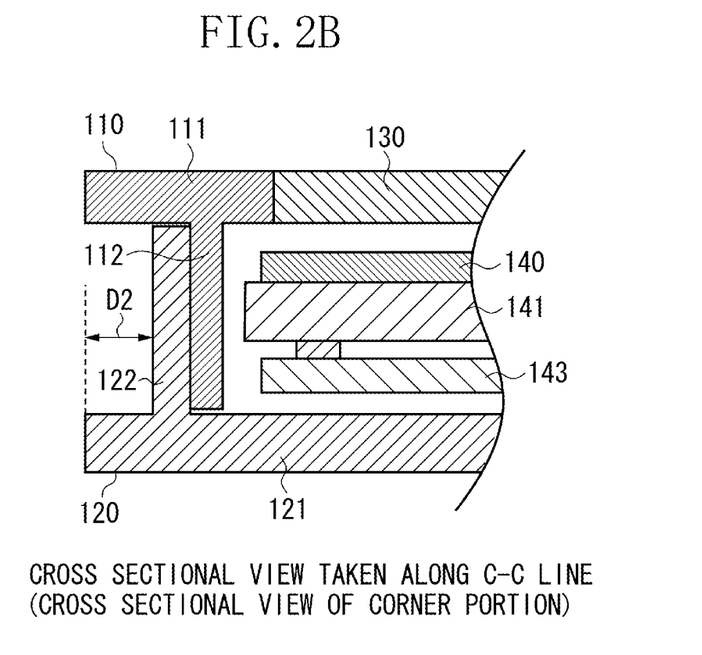

With reference to FIGS. 2A and 2B, a structure according to the present exemplary embodiment that provides sufficient shock resistance to the X-ray imaging apparatus 100 is described. FIGS. 2A, 2B illustrate cross sections of a peripheral edge portion of the X-ray imaging apparatus 100. FIG. 2A is a cross sectional view taken along the line B-B in FIG. 1A, illustrating a cross section of a side of the X-ray imaging apparatus 100. FIG. 2B is a cross sectional view taken along the line C-C in FIG. 1A, illustrating a cross section of a corner portion of the X-ray imaging apparatus 100.

As illustrated in FIGS. 2A and 2B, a recess is formed along the sides and the corner portions of the X-ray imaging apparatus 100, along at the approximately center in the thickness direction. More specifically, the front casing 110 has a side wall 112, and the rear casing 120 has a side wall 122, the side walls 112 and 122 each having a protruding step at one end, so that a recess is formed when the front casing 110 is combined with the rear casing 120.

The recess has a length extending from the inner side surface of the front planer portion 111 to the inner side surface of the rear planer portion 121. Without the recess, an impact load applied to the sides and the corner portions are received by the entire side walls 112 and 122, which generates a bending moment corresponding to the entire height of the side walls 112 and 122.

The structure of the present exemplary embodiment provides a recess which will not be in contact with the floor at dropping of the X-ray imaging apparatus 100, and thereby an impact load applied to the sides and the corner portions are received by the front planer portion 111 and the rear planer portion 121. In other words, the impact causes only a compressive load applied to the planer portions 111 and 121 without bending moment, which unlikely results in deformation of the casings 110 and 120.

The structure provides sufficient shock resistance property to the X-ray imaging apparatus 100. The recess has a depth of about 0.5 to 1.5 mm, which provides a narrower casing trim as compared to the case using a buffer material.

Depths of the recess along the sides and corner portions are described. The corner portions each have a narrower area than that of the sides to be brought into contact with a floor when the X-ray imaging apparatus 100 is dropped. This often causes deformation of the floor hit by the apparatus 100, and the deformed portion of the floor may contact the recess with load.

The load applied to the recess generates a bending moment at the side walls 112 and 122, leading to deformation of the casings 110 and 120. Therefore, the recess needs to have a large depth to definitely make the recess a non-contact area, so that the risk of deformation of the apparatus 100 when a load is applied can be reduced. Since the narrow casing trim is achieved, the distances from the X-ray sensor panel 140 to the outermost surface of the casings 110 and 120 are small and a sufficient depth for the recess is not available along the sides, but a relatively large depth is available at the corner portions. From the above reasons, the recess at the corner portions may desirably have a depth D2 larger than a depth D1 along the sides.

Figure 3:
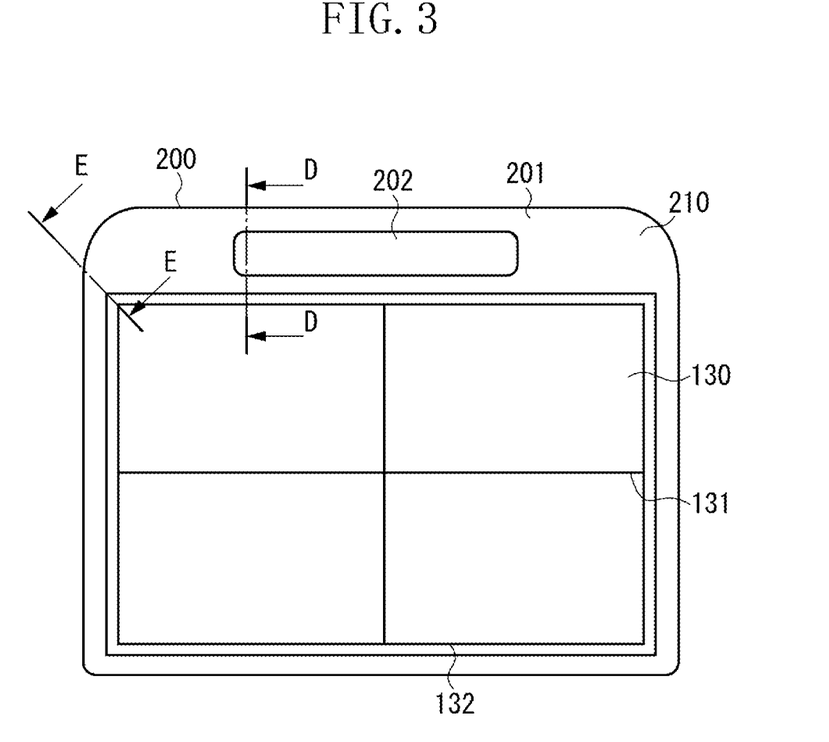
FIG. 3 illustrates an X-ray imaging apparatus according to a second exemplary embodiment.

An X-ray imaging apparatus according to a second exemplary embodiment is described, which has a gripping portion along one side thereof. The gripping portion reduces burden of a person who is carrying it, and improves portability of the X-ray imaging apparatus. FIG. 3 illustrates an X-ray imaging apparatus 200 according to the present exemplary embodiment. The X-ray imaging apparatus 200 has a gripping portion 201 and an opening 202, in the upper part of FIG. 3, so that a person can grip the gripping portion 201 to carry the X-ray imaging apparatus 200.

Figure 4A:
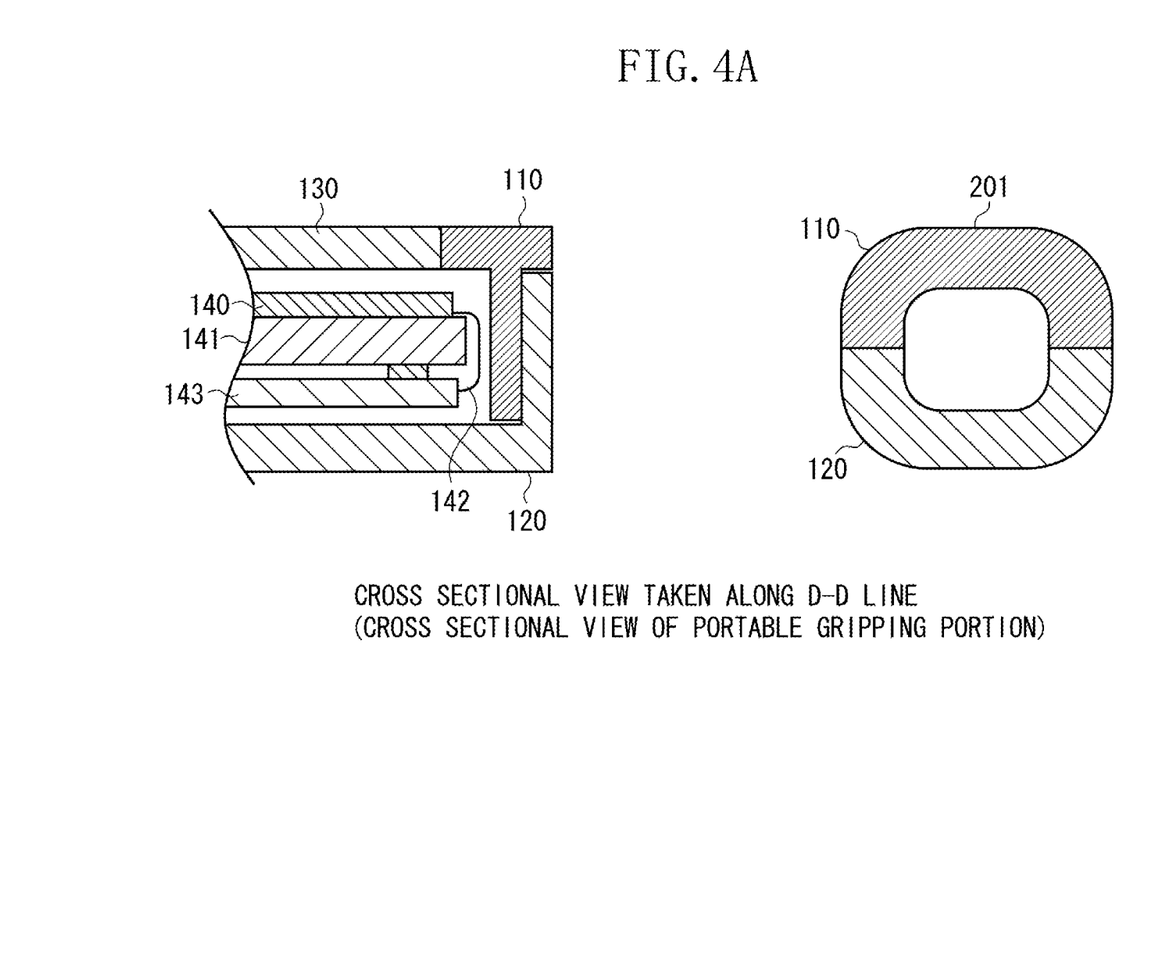
FIGS. 4A and 4B are cross sectional views each illustrating a peripheral edge portion of the X-ray imaging apparatus according to the second exemplary embodiment.
Figure 4B:
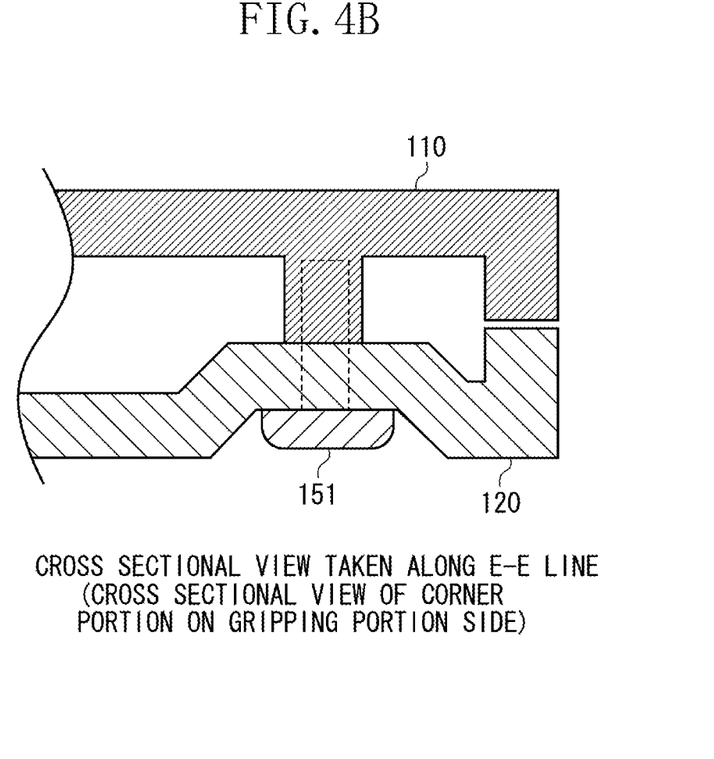

A cross section of the peripheral edge portion of the side with the gripping portion is described. FIG. 4A is a cross sectional view taken along the line D-D in FIG. 3. FIG. 4B is a cross sectional view taken along the line E-E in FIG. 3. The gripping portion 201 is formed with the front casing 110 and the rear casing 120, and has corner portions formed in a shape easy to grip through rounding processing.

The part of the front casing 110 and the rear casing 120 forming the gripping portion 201 is not limited in its outer size, and can have a thickness that provides a sufficient strength to the part. The part may be formed with a buffer material (not illustrated) as needed. At positions near the corner portions, the front casing 110 may be fastened to the rear casing 120 with screws 151 to prevent deformation.

When a person carries the X-ray imaging apparatus 200, the gripping portion 201 is kept upward, and thereby if the person accidentally drops the X-ray imaging apparatus 200, the gripping portion 201 rarely drops first toward the ground. Therefore, the gripping portion 201 does not need to have a recess along its side and the corner portions. The gripping portion 201 with no steps provides a user a shape comfortable to touch.

Figure 5:
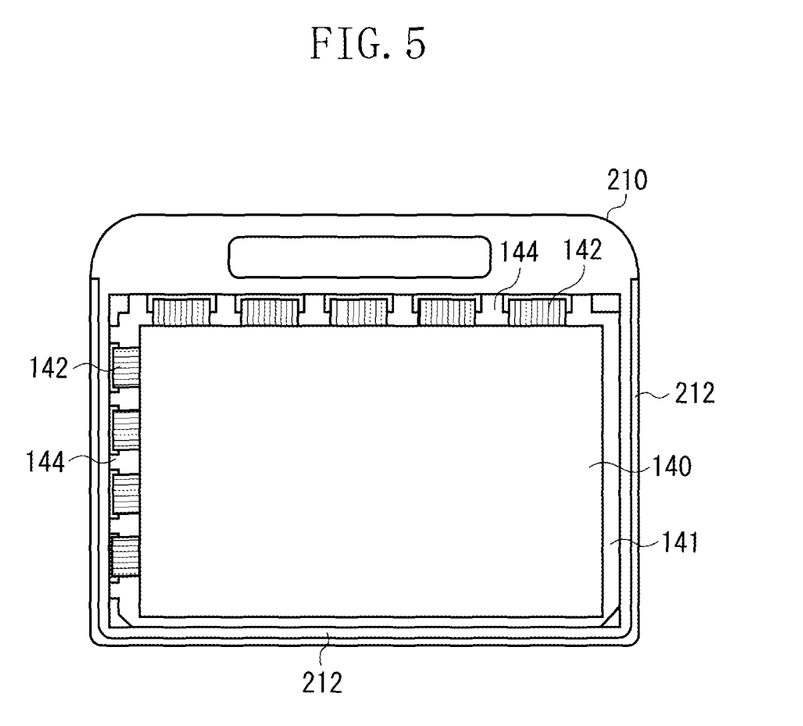
FIG. 5 illustrates an inner structure of the X-ray imaging apparatus according to the second exemplary embodiment.

An inner structure of the casings 110 and 120 of the X-ray imaging apparatus 200 is described. FIG. 5 illustrates an inner structure of the X-ray imaging apparatus 200, with the front casing 110 being removed. An X-ray sensor panel 140 attached to the supporting member 141 is incorporated in the casings 110 and 120. The supporting member 141 may desirably be larger than the sensor panel 140 so that the sensor panel 140 does not extend beyond the supporting member 141. The supporting member 141, not the sensor panel 140, is brought into contact first with the inner side wall of the casing in case of dropping, which can prevent breakage of the glass.

In the present exemplary embodiment, the supporting member 141 has a circumference located with a small gap of 1 mm or less from the inner side wall of the casing. The supporting member 141 is fixed inside of the casing by fitting. The fixing by fitting reduces the number of screws used, as compared to the case where the supporting member 141 is fixed by screws to the casings.

The sensor panel 140 has a plurality of flexible circuit boards 142 along its two sides. To prevent the flexible circuit boards 142 from being sandwiched between the side wall of the casing and the supporting member 141, the supporting member 141 has a plurality of convex portions 144. The convex portions 144 may be separate components attached to the supporting member 141. The convex portions 144 are disposed between the flexible circuit boards 142. As a result, a plurality of sides of the convex portions 144 is in contact with the side wall, which can prevent deformation of the convex portions 144 at supporting of weights of the X-ray sensor panel 140 and the supporting member 141.

When the X-ray imaging apparatus 200 is dropped, the drop of the supporting member 141 and the X-ray sensor panel 140 can be supported by the inner side of the side wall of the casing. Accordingly, an impact load is applied to the inner side of the side wall of the casing. A recess formed along the side wall of the casing may be a cause to deform the casing due to the impact load applied from inside thereof.

The above deformation occurs because the impact load applied from the inside of the side wall cannot be received and supported from the outside of the side wall. The thickness of the side wall reduced to form the recess is another factor of the deformation. In particular, the corner portions each have a small area to receive the load, and the side wall at the corner portions may have a smaller thickness to form a deeper recess.

In view of the above structure, at the corner portions having a recess, the supporting member 141 may desirably be separately located from the inner side of the side wall of the casing. This eliminates supporting of the supporting member 141 and the X-ray sensor panel 140 at the inside of the side wall at the corner portions that cannot endure the impact load applied from the inside, decreasing the risk of deformation of the casing.

The above structure may be preferably applied in particular to the case where the supporting member 141 is fixed to the casing without screws, and held movably by fitting as in the present exemplary embodiment, because the weights of the supporting member 141 and the sensor panel 140 are supported only by the inner side of the side wall of the casing.

Figure 6:
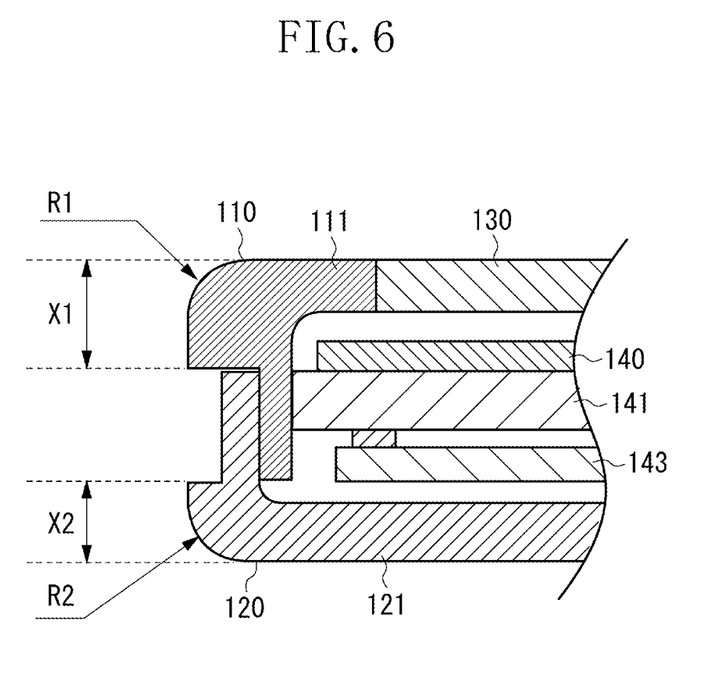
FIG. 6 is a cross sectional view illustrating a peripheral edge portion of an X-ray imaging apparatus according to a third exemplary embodiment.

A case is described where the corner portions formed with the sides and the front and rear surfaces of a casing are treated by rounding processing. FIG. 6 is a cross sectional view illustrating an X-ray imaging apparatus of a third exemplary embodiment. The corner portions of the casing are treated by rounding processing to have a radius of curvature of about 1.0 to 3.0 mm, for user portability and aesthetic appearance of the apparatus.

If the radius of curvature is larger than the thicknesses of the front planer portion 111 and the rear planer portion 121, the impact load applied from the sides and the corner portions cannot be received only by the front planer portion 111 and the rear planer portion 121, generating a bending moment on the side wall of the casing. The bending moment is proportional to the total value of $X1+R1$, where $R1$ is the radius of curvature of the outer angle of the front casing 110, and $X1$ is the distance to the recess from the front surface of the X-ray imaging apparatus. Reduction in the bending moment can be achieved with a larger recess and a smaller $X1$.

Herein, only the front casing 110 is used for detail description, since the same thing can be said for the rear casing 120. The front casing 110 can be said to have a structure with a required mechanical strength when satisfying an expression: $X1+R1 \leq B1/C1$, where $B1$ is a coefficient representing the strength of the front casing 110, and $C1$ is a coefficient representing a required shock resistant property. The value $B1$ depends on a material, a shape of the front casing 110, a thickness of the front planer portion 111, and a thickness of the side wall, and the value $C1$ depends on an impact energy caused by dropping.

The value $B1$ can be obtained through simulations and experiments, and in a simpler way, can be calculated as a value proportional to the cube of the thickness (i.e., the value obtained by multiplying the cube of the thickness by a predetermined coefficient). The value $C1$ can be calculated as a value proportional to a height from which the X-ray imaging apparatus is supposed to be dropped and the weight of the apparatus (i.e., the value obtained by multiplying a predetermined coefficient).

For example, in a case where the X-ray imaging apparatus having a weight of 3 kg is dropped from a 1-m height, and the casing of the apparatus is made of magnesium and includes a planer portion having a thickness of about 1.5 mm and a side wall having a thickness of about 2.0 mm, the value $B1/C1$ obtained through experiments becomes about 6. In other words, when the total value of $X1+R1$ is 6 mm or more, plastic deformation occurs in the casing, which may cause problems such as poor image quality due to light entrance to the casing and non-accommodation of the X-ray imaging apparatus into a mount due to increase in thickness of part of the casing.

The value $C1$ is proportional to the height the apparatus drops from, and thereby a height reduced to a half doubles the value $B1/C1$. Accordingly, the total value $X1+R1$ of 12 mm or less can satisfy the drop impact resistance required for the X-ray imaging apparatus.

The planer area width of the sides of the casing is represented by a difference value of $X1-R1$, and needs to be equal to or greater than a predetermined value (e.g., $A1$). The value $A1$ depends on production tolerance and a gate width required for die casting, for example.

As described above, when the values $X1$ and $X2$ satisfy the expression $Rn+An \leq Xn \leq Bn/Cn-Rn$ ($n=1, 2$), an X-ray imaging apparatus can be obtained with a strength required even when the corner portions thereof are treated by rounding processing for portability and aesthetic appearance.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2011-211128 filed Sep. 27, 2011, which is hereby incorporated by reference herein in its entirety.

What is claimed is:

1. An X-ray imaging apparatus, comprising:
   an X-ray sensor configured to convert an X-ray to an image signal;
   a supporting member configured to support the X-ray sensor; and a casing having the X-ray sensor and the supporting member incorporated therein, wherein the casing includes a front casing configured to cover a front surface of the X-ray imaging apparatus where an X-ray enters, and a rear casing configured to cover a rear surface opposite the front surface of the X-ray imaging apparatus, wherein the casing includes corner portions and sides, and wherein recesses along each of the corner portions of the casing and recesses along each of the sides of the casing are formed on the exterior of the casing at a connection portion of the front casing and the rear casing, and a depth of the recesses along each of the corner portions of the casing is larger than a depth of the recesses along each of the sides of the casing.

2. The X-ray imaging apparatus according to claim 1, further comprising a gripping portion on at least one side of the apparatus for portability, and wherein the recesses extending along the side having the gripping portion and the corner portions on the side having the gripping portion have a depth smaller than that of the recesses extending along the side opposite the side having the gripping portion and the corner portions on the opposite side.

3. The X-ray imaging apparatus according to claim 1, wherein the supporting member and the X-ray sensor at the corner portions of the casings are individually separately located from an inner surface of a side wall of the casings.

4. The X-ray imaging apparatus according to claim 3, wherein the supporting member and the X-ray sensor are held inside the casings in a movable manner relative to the casings.

5. The X-ray imaging apparatus according to claim 1, wherein the distance from a planer portion of the front casing and/or the rear casing to the recesses is larger than a radius of curvature of the corner portions of the front casing and/or the rear casing.

6. The X-ray imaging apparatus according to claim 5, wherein the distance from the surface of the planer portion of the front casing and/or the rear casing to the recesses satisfies the expression $R+A \leq X \leq B/C-R$, wherein X is the distance, R is the radius of curvature of the corner portions of the front casing or the rear casing, A is a coefficient determined based on production process of the apparatus, B is a coefficient representing a strength of the casing, and C is a coefficient representing a shock resistant property required for the apparatus.

7. An X-ray imaging apparatus, comprising:

an X-ray sensor configured to convert an X-ray to an image signal;

a supporting member configured to support the X-ray sensor; and a casing having the X-ray sensor and the supporting member incorporated therein, a gripping portion on at least one side of the apparatus for portability, wherein the casing includes a front casing configured to cover a front surface of the X-ray imaging apparatus where an X-ray enters, and a rear casing configured to cover a rear surface opposite the front surface of the X-ray imaging apparatus, wherein the casing includes corner portions and sides, wherein recesses along each of the corner portions of the casing and recesses along each of the sides of the casing are formed toward the exterior of the casing at a connection portion of the front casing and the rear casing, and wherein the recesses along each of the corner portions has a depth smaller than that of the recess along the side of the casing opposite the side having the gripping portion.

8. An X-ray imaging apparatus, comprising:

an X-ray sensor configured to convert an X-ray to an image signal;

a supporting member configured to support the X-ray sensor; and a casing having the X-ray sensor and the supporting member incorporated therein, wherein the casing includes a front casing configured to cover a front surface of the X-ray imaging apparatus where an X-ray enters, and a rear casing configured to cover a rear surface opposite the front surface of the X-ray imaging apparatus, wherein the casing includes corner portions and sides, and wherein recesses along at least two corner portions of the casing and recesses along at least two sides of the casing are formed on the exterior of the casing at a connection portion of the front casing and the rear casing, and a depth of the recesses along at least two corner portions of the casing is larger than a depth of the recesses along at least two sides of the casing.

* * * * *